United States Patent [19]
Hall

[11] Patent Number: 5,840,289
[45] Date of Patent: Nov. 24, 1998

[54] ANTIPERSPIRANT AEROSOL COMPOSITION AND METHOD OF MAKING SAME

[75] Inventor: Peter John Hall, Bromborough, United Kingdom

[73] Assignee: Chesebrough-Pond's USA Co., Division of Conopco, Inc., Greenwich, Conn.

[21] Appl. No.: 804,872

[22] Filed: Feb. 24, 1997

[30] Foreign Application Priority Data

Feb. 29, 1996 [GB] United Kingdom ............... 9604340

[51] Int. Cl.$^6$ .............. A61K 7/38; A61K 7/32; A61K 7/00
[52] U.S. Cl. .............. 424/68; 424/65; 424/400; 424/401
[58] Field of Search .............. 424/65, 68, 400, 424/401

[56] References Cited

U.S. PATENT DOCUMENTS

| | | | |
|---|---|---|---|
| 3,974,270 | 8/1976 | Kenkare et al. | 424/47 |
| 4,122,029 | 10/1978 | Gee et al. | 252/309 |
| 4,265,878 | 5/1981 | Keil | 424/68 |
| 4,822,596 | 4/1989 | Callingham et al. | 424/46 |
| 4,904,463 | 2/1990 | Johnson et al. | 424/44 |

FOREIGN PATENT DOCUMENTS

| | | |
|---|---|---|
| 0 006 738 | 1/1980 | European Pat. Off. . |
| 0 006 739 | 1/1980 | European Pat. Off. . |
| 0 007 191 | 1/1980 | European Pat. Off. . |
| 0 256 832 | 2/1988 | European Pat. Off. . |
| 0 274 252 | 7/1988 | European Pat. Off. . |
| 0 191 628 | 8/1988 | European Pat. Off. . |
| 0 295 071 | 12/1988 | European Pat. Off. . |
| 0 207 605 | 3/1989 | European Pat. Off. . |
| 0 334 203 | 9/1989 | European Pat. Off. . |
| 0 491 395 | 6/1992 | European Pat. Off. . |
| 0 499 398 | 8/1992 | European Pat. Off. . |
| 0 537 003 | 4/1993 | European Pat. Off. . |
| 0 570 085 | 11/1993 | European Pat. Off. . |
| 0 595 339 | 5/1994 | European Pat. Off. . |
| 0 665 007 | 8/1995 | European Pat. Off. . |
| 1013386 | 4/1963 | United Kingdom . |
| 1111867 | 11/1965 | United Kingdom . |
| 1568831 | 6/1980 | United Kingdom . |
| 1597497 | 9/1981 | United Kingdom . |
| 1597498 | 9/1981 | United Kingdom . |
| 2291805 | 2/1996 | United Kingdom . |
| 95/31967 | 11/1995 | WIPO . |

*Primary Examiner*—Shelley A. Dodson
*Attorney, Agent, or Firm*—Milton L. Honig

[57] ABSTRACT

A suspension antiperspirant aerosol composition for topical application to the human skin comprising 1–30% by weight of solid activated aluminium chlorohydrate, 1–30% by weight of a liquid masking agent 30–90% of a propellant for expelling the composition from a container and a carrier.

6 Claims, No Drawings

ANTIPERSPIRANT AEROSOL COMPOSITION AND METHOD OF MAKING SAME

BACKGROUND OF THE INVENTION

1. Field of the Invention

This invention relates to aerosol antiperspirant compositions suitable for topical application to the human skin.

2. The Related Art

Antiperspirant compositions suitable for topical application typically contain an antiperspirant material such as aluminum chlorohydrate which acts to suppress the level of perspiration on the area of the body to which it is applied. Antiperspirant compositions are widely applied in the form of a pressurized propellant driven aerosol spray.

Aerosol antiperspirant compositions typically have the antiperspirant material suspended in an anhydrous vehicle together with a propellant and a suspending agent. Other minor ingredients can also be present, and the composition is housed in a pressurised container.

A major problem associated with all antiperspirants, including aerosol antiperspirants, is that of deposition or whitening where the antiperspirant active, which is usually in powder form, is deposited on a user's clothes or skin thereby causing visible whitening/staining and occasionally damage to the clothes.

Various attempts have been made to reduce the whitening or visible deposits. A widely used approach has been to incorporate masking oils such as aliphatic hydrocarbons, esters and siloxane fluids into antiperspirant formulations.

Generally, the masking oils also have an emollient effect.

The masking oils function by coating the surface of the antiperspirant active particles to minimise scattering of light, thereby rendering the active less visible to the naked eye.

The masking method has been found to reduce whitening in stick and roll-on products. However, the reduction of whitening in aerosol compositions containing activated aluminium chlorohydrate (AACH) as the active has been less effective.

It has proven particularly difficult to match the Refractive Index (RI) of the masking oil with that of AACH, as commercially available AACH does not have a continuous RI value throughout the particle. More particularly, AACH particles generally contain hollow cores, having an RI of 1.0 while the RI of the outer particle is in the region of 1.5 which results in visible whitening.

An object of the invention is to provide an improved aerosol antiperspirant composition, particularly one comprising a particulate antiperspirant active, having reduced visible whitening.

A further object of the invention is to provide a method for producing an antiperspirant composition having reduced visible whitening.

SUMMARY OF THE INVENTION

According to the invention there is provided a suspension antiperspirant aerosol composition for topical application to the human skin comprising 1–30% by weight of solid or non-hollow activated aluminium chlorohydrate, 1–30% by weight of a liquid masking agent, 30–90% of a propellant for expelling the composition from a container and a carrier.

DETAILED DESCRIPTION OF THE INVENTION

Preferably, the activated aluminium chlorohydrate comprises non-hollow particles. By "non-hollow" in this context is meant particles which contain no cores or voids which have a diameter of greater than 40% of the particle diameter. Preferably, any cores or voids are less than 30% of the particle diameter, more preferably less than 20% of the particle diameter, even more preferably less than 10% of the particle diameter, most preferably less than 5% of the particle diameter. Suitably, the activated aluminium chlorohydrate has a continuous Refractive Index. Preferably, the aluminium chlorohydrate has a Refractive Index of 1.52 to 1.57 and the masking agent has a Refractive Index of 1.40 to 1.57.

A preferred method of obtaining such AACH with no or very small cores or voids is to obtain AACH with very large particle sizes (e.g. 100 microns or more), and reduce these particles in size by grinding or milling them.

More preferably, the masking agent is selected from the group comprising benzoate esters, hydrogenated polybutene, PPG-14 butyl ether, isopropyl palmitate, phenylsilicone and isopropylmyristate.

In an alternative embodiment the invention relates to the use of a solid (i.e. non-hollow) activated aluminium chlorohydrate in the preparation of an antiperspirant composition.

AACH antiperspirant actives and method for producing same suitable for use in the present invention are described in GB 1,568,831, GB 1,597,497, GB 1,597,498, EP 6,738, EP 6,739, EP 7,191, EP 191,628, EP 256,832 and EP 491,395 the contents of which are incorporated herein by reference.

The particulate material is suspended in a hydrophobic emollient liquid masking agent. The masking agent improves initial adhesion of the antiperspirant active to the skin, thus aiding in the capture of the antiperspirant material by the skin as it is dispensed in spray form. Also, the agent serves as a diluent, lubricant or spreading agent to facilitate uniform distribution of the antiperspirant material on the skin.

Suitable emollient liquid masking agents are disclosed in U.S. Pat. Nos. 4,822,596 and 4,904,463, the disclosure of which are specifically incorporated by reference herein. The amount of emollient liquid masking agent in the composition according to the invention may preferably vary from 1–30% by weight of the total composition.

Preferred emollient masking agents are the Finsolv (Trade Mark) Benzoate Esters available from Finstex Inc. and Panalane, a hydrogenated polybutene, available from Amoco, Fluid AP (Union Carbide), isopropyl palmitate, phenylsilicone, and isopropyl myristate.

In an alternative embodiment of the invention, the liquid emollient carrier element of the composition comprises a volatile silicone fluid. Preferred volatile fluids for use in compositions according to the invention include dimethyl cyclosiloxanes, such as DC244, DC245, DC344 and DC345 fluids (Dow Corning).

In order to prevent caking or settling out of the antiperspirant salt in the hydrophobic emollient liquid carrier, a bulking or suspending agent is preferably incorporated into the composition of the invention. The suspending agent is preferably a hydrophobically treated montmorillionite clay such as bentonites and hectorites. One such commercially available clay is Bentone-38, which is hectorite clay available from NL Industries, Inc. The amount of clay in the composition of the invention may preferably vary from 0.2–5.0% by weight of the total composition.

The propellant gas according to the invention can be any liquefiable gas known in the art for use in propellant driven aerosol containers. Examples of suitable propellants include trichlorofluoromethane, trichlorotrifluoromethane, difluoroethane, propane, butane or isolbutane or combinations thereof. The amount of propellant in the composition of the invention is conveniently no more than 90 wt %.

Other minor ingredients which can be present in compositions according to the invention include:

- cosmetically acceptable vehicles, such as straight and branched chain alcohols, for example, ethanol, isobutanol or isopropanol;
- deodorant active perfumes and deodorant compounds which can act as antimicrobial agents;
- hydrophobic oils, such as liquid paraffin oils;
- inorganic electrolytes, such as sodium chloride or sodium sulphate;
- other thickeners such as clays, silicas, for example, Aerosil 200 and hydroxypropyl celluloses such as Klucel;
- polar additives such as propylene carbonate or alcohol;
- skin feel improvers, such as talc and finely divided polyethylene such as Accumist B18;
- humectants, such as polyols, for example glycerol;
- perfumes;
- preservatives and antioxidants;
- skin benefit agents such as allantoin;
- colours;
- other cosmetic adjuncts conventionally employed in propellant driven aerosol products.

Whilst not wishing to be bound by any theory Applicant believes that the poor masking associated with the aerosol antiperspirant compositions of the prior art is due to the morphology of the antiperspirant actives used in aerosol compositions.

The active used in suspension stick and roll-on products is AZAG. AZAG particles are irregular in shape and have a mean particle diameter of about 2 microns. The particles are solid in nature and are obtained from milling larger particles. The "whiteness" of skin deposits using suspension stick and roll-on products is usually more intense than for aerosol due to the use of the smaller particle sizes in such products which causes more light scattering surfaces to be exposed to the light.

Smaller particle sizes are used to avoid settling out of the active during setting of stick antiperspirants and with roll-ons to facilitate resuspension. Conversely, larger macro-spherical actives are utilized in aerosol formulations partly for reasons of safety.

The favoured aerosol active is AACH, in the form of near-spherical particles of mean diameter for example 20–30 microns, which can be produced by reducing in particle size particles which originally had a size in the region of 100 microns. The original particles have a hollow core i.e. are in the form of a shell enclosing a hollow air-containing core. Masking oils help to eliminate whitening as previously described. However, it is believed that while the refractive index of the oil can be matched with the particle shell to reduce visible masking a refractive index mismatch between the shell and the hollow core remains. Hence processing to remove the hollow core, and hence the differential in Refractive Indices, is beneficial.

More particularly, the antiperspirant active has a Refractive Index (RI) of 1.52–1.57, that of the oils is 1.40–1.57, and the RI of air is 1.00. It is believed that the core-shell interface acts as the main scattering source in the presence of the oil to cause the excessive visible whitening experienced with aerosol formulations.

EXAMPLES

The invention will now be further described by way of example only. The following compositions were prepared using standard techniques known in the art.

1. Comparative

A supplier produce solid (i.e. no entrapped air) aluminium chlorohydrate Locron S (ex Hoechst) active of large particle size (e.g. around 100 microns) was milled down to a mean particle size of 30 microns, which is comparable with that of an AACH active (ex Giuilini), and these were combined with four masking oils to determine the percentage whiteness reduction.

The whiteness measurement is that obtained for a sprayed deposit (i.e. active) weight of 0.2 g.

The results are given in the table below. The results show that the level of whiteness (as measured using digital image analysis under controlled lighting conditions) for the two actives (AACH and milled ACH) are very close in the absence of masking oil. In the presence of oils the level of whiteness of the ACH is, in all cases, less than that of the AACH. The percentage whiteness reduction is given in brackets.

| | No Oil | Finsolv TN | Silkflo 364NF | Panalene L-14E | Cosmacol PLG |
|---|---|---|---|---|---|
| AACH | 27500 | 17000 (38%) | 18380 (33%) | 21130 (23%) | 15200 (55%) |
| ACH | 26750 | 12500 (53%) | 16250 (39%) | 16250 (39%) | 5000 (81%) |

It should be noted that the refractive indices of the AACH and ACH are 1.52 and 1.53 respectively. Accordingly, differences in masking cannot be explained by a differences in the RI values of the actives.

Accordingly, a milled AACH particle which is solid i.e. does not contain a hollow core or is not a hollow spheroid particle would clearly result in reduced whitening.

The AACH active could be prepared as described in the aforementioned references incorporated herein.

2. Compositions

A packaged propellant driven aerosol antiperspirant composition was prepared having the following formulation:

| FORMULATION | |
|---|---|
| ACH/AACH | 10% |
| Bentone 38 | 1% |
| Volatile silicone Q2/1465 | 3.5% |
| Perfume | 0.5% |
| CAP 30 | 75% |
| Masking Oil | 10% |

The masking oils were substituted into the formulation at a level of 10% replacing 10% of the volatile silicone.

3. Whiteness Reduction

The following example shows the results of varying in a standard antiperspirant aerosol composition the level of a masking agent fluid and antiperspirant active, in particular with regard to the morphology of the antiperspirant active. The "base" composition for the aerosol contained the amounts of masking agent and antiperspirant active shown along with 13% volatile silicone, 1% Bentone 38, and the balance being bentone/propane/isobutane propellant.

In such a sprayed aerosol composition, under consistent spray and observation conditions, a Quantitative Descripter Analysis (QDA) score was attributed to various aerosol formulations in which the level of masking fluid and nature of antiperspirant salt was varied.

| Antiperspirant Active | % Fluid AP (MASKING AGENT) | QDA Deposits Score |
|---|---|---|
| 10% AACH (conventional) | 0 | 57 |
| 10% AACH (conventional) | 6 | 56 |
| 10% AACH (conventional) | 10 | 51 |
| 10% ACH | 6 | 38 |
| 10% milled AACH | 6 | 15 |

The results show that the addition of increasing levels of masking agent to normal AACH (having a hollow core) has a relatively small effect on perceived whiteness. However by milling the AACH and thereby eliminating the hollow core of AACH particles, a large reduction in perceived whiteness is observed. The reduced whiteness of ACH compared to AACH further emphasises the importance of the hollow core in AACH particles in determining perceived whiteness.

4. Whiteness Reduction

Again a standard antiperspirant aerosol composition containing varying amounts of antiperspirant active and masking fluid in the same aerosol base as described in Example 3. The whiteness was measured by image analysis techniques. The figures in parentheses indicate the change in whiteness compared to the standard of 10% hollow AACH with no masking oil.

| | Masking Oil (% w/w) | | |
|---|---|---|---|
| Formulation | 0 | 6 | 10 |
| 10% AACH | 27500 | 24000 (−16.6) | 17000 (−38%) |
| 10% ACH | 26750 (−3%) | — | 12,5000 (−55%) |
| 10% milled AACH | 30,800 (+12%) | 12780 (−54%) | — |

Hence the figures indicated that with milled AACH, a huge reduction in whiteness can be attained for the use of relatively little masking oil compared with similar formulations containing ACH and unmilled AACH.

I claim:

1. A suspension antiperspirant aerosol composition for topical application to the human skin comprising 1–30% by weight of solid milled activated aluminium chlorohydrate, 1–30% by weight of a liquid masking agent 30–90% of a propellant for expelling the composition from a container and a carrier.

2. An aerosol composition as claimed in claim 1 wherein the activated aluminium chlorohydrate comprises non-hollow particles.

3. An aerosol composition as claimed in claim 1 wherein the activated aluminium chlorohydrate has a continuous Refractive Index.

4. An aerosol composition as claimed in claim 1 wherein the activated aluminum chlorohydrate has a Refractive Index of 1.52 to 1.57.

5. An aerosol composition as claimed in claim 1 wherein the masking agent has a Refractive Index of 1.40 to 1.57.

6. An aerosol composition as claimed in claim 1 wherein the masking agent is selected from the group comprising benzoate esters, hydrogenated polybutene, PPG-14 butyl ether, isopropyl palmitate, phenylsilicone and isopropylmyristate.

* * * * *